United States Patent
Rodriguez et al.

(10) Patent No.: US 10,729,649 B2
(45) Date of Patent: Aug. 4, 2020

(54) COSMETIC NANOEMULSION

(71) Applicant: TOTAL MARKETING SERVICES, Puteaux (FR)

(72) Inventors: Corinne Rodriguez, Beauvais (FR); Harmonie Magniez, Nointel (FR); Daniel Colletta, La Trinité de Thouberville (FR); Serge Quillet, Viroflay (FR); Benjamin Swoboda, Orgeval (FR)

(73) Assignee: TOTAL MARKETING SERVICES, Puteaux (FR)

( * ) Notice: Subject to any disclaimer, the term of this patent is extended or adjusted under 35 U.S.C. 154(b) by 0 days.

(21) Appl. No.: 15/572,141

(22) PCT Filed: May 3, 2016

(86) PCT No.: PCT/EP2016/059849
§ 371 (c)(1),
(2) Date: Nov. 6, 2017

(87) PCT Pub. No.: WO2016/177704
PCT Pub. Date: Nov. 10, 2016

(65) Prior Publication Data
US 2018/0125766 A1 May 10, 2018

(30) Foreign Application Priority Data
May 4, 2015 (FR) .................................... 15 53980

(51) Int. Cl.
A61K 8/06 (2006.01)
A61K 8/31 (2006.01)
A61Q 19/00 (2006.01)
A61K 9/107 (2006.01)
A61K 47/06 (2006.01)

(52) U.S. Cl.
CPC ............ *A61K 9/1075* (2013.01); *A61K 8/062* (2013.01); *A61K 8/31* (2013.01); *A61K 47/06* (2013.01); *A61Q 19/00* (2013.01); *A61K 2800/10* (2013.01); *A61K 2800/21* (2013.01)

(58) Field of Classification Search
None
See application file for complete search history.

(56) References Cited

U.S. PATENT DOCUMENTS

2003/0007986 A1 1/2003 Stora et al.
2007/0241306 A1 10/2007 Wehner et al.
2009/0123398 A1* 5/2009 Laba ................. A61K 8/31 424/59
2009/0176876 A1 7/2009 Ramirez et al.
2009/0208541 A1* 8/2009 Gesztesi .............. A61K 8/06 424/401
2012/0171263 A1* 7/2012 Capelas Romeu ...... A61K 8/06 424/401
2013/0289136 A1 10/2013 Paufique

FOREIGN PATENT DOCUMENTS

| JP | H02-295912 A | 12/1990 |
| WO | 02/032390 A1 | 4/2002 |
| WO | 2007/095255 A2 | 8/2007 |
| WO | 2010-085753 A1 | 7/2010 |
| WO | 2012/085491 A1 | 6/2012 |

OTHER PUBLICATIONS

Shinoda et al., "The Stability of O/W Type Emulsions as Functions of Temperature and the HLB of Emulsifiers: The Emulsification by PIT-method," Journal of Colloid and Interface Science, Jun. 1969, vol. 30, No. 2, pp. 258-263.
Mitsui et al., "An Application of the Phase-inversion-temperature Method to the Emulsificaiton of Cosmetics. I. Factors Affecting the Phase-inversion Temperature", Bulletin of the Chemical Society of Japan, vol. 43, No. 10, pp. 3044-3048, 1970.
Förster et al., "Calculation of optimum emulsifier mixtures for phase inversion emulsification", International Journal of Cosmetic Science, 16(2), pp. 84-92, 1994.
Tadros et al., "Formation and stability of nano-emulsions", Advances in Colloid and Interface Science, pp. 303-318, 2004.
Babu et al., "Assessment of skin irritation and molecular responses in rat skin exposed to nonane, dodecane and tetradecane", College of Pharmacy and Pharmaceutical Sciences, pp. 255-266, 2004.
Sato et al., "The Effect of Combination of Various Oils, Emulsifiers and Additives on the Phase Inversion Temperature in Emulsion Systems", Bulletin of the Chemical Society of Japan, 43(10), pp. 3044-3048, 1970.
ICI Americas Inc., "The HLB system. A time-saving guide to Emulsifier Selection" Ch.1-8, pp. 1-22, 1980.
Nov. 8, 2016 International Search Report issued in International Patent Application No. PCT/EP2016/059849.
Nov. 7, 2017 Written Opinion issued in International Patent Application No. PCT/EP2016/059849.

* cited by examiner

Primary Examiner — Bethany P Barham
Assistant Examiner — Dominic Lazaro
(74) Attorney, Agent, or Firm — Oliff PLC

(57) ABSTRACT

A cosmetic or dermatological composition in the form of an oil-in-water nanoemulsion, including: a lipophilic phase (a) including at least one hydrocarbonated oil comprising at least one isoparaffin, and at least one cycloalkane, an emulsifying system (b) including at least one non-ionic emulsifier, and an aqueous phase (c), where the ratio between the lipophilic phase (a) and the emulsifying system (b) is higher than, or equal to, 0.5 in terms of weight.

19 Claims, No Drawings

COSMETIC NANOEMULSION

FIELD OF THE INVENTION

The invention relates to a cosmetic or dermatological composition in the form of an oil-in-water nanoemulsion obtained via the phase inversion temperature technique.

The invention also relates to the uses of said composition.

TECHNICAL CONTEXT OF THE INVENTION

It is common practice to use oil-in-water (O/E) emulsions in the cosmetic and dermatological fields. These emulsions, which are constituted of a lipophilic phase (also known as the oily phase or fatty phase) dispersed in an aqueous phase, have, as a result, an outer aqueous phase and are thus products that are pleasant to use, on account of the sensation of freshness that they afford. The manufacture of direct emulsions that are concentrated in oil is often difficult and the emulsions obtained are often unstable.

These emulsions are conventionally obtained mechanically, for example by emulsification with a rotor-stator or by means of a high-pressure homogenizer, substantial energy input being necessary to divide the dispersed phase into small drops. To stabilize these emulsions, nonionic emulsifiers the oil-in-water (O/W) type, i.e. with an HLB (hydrophilic-lipophilic balance) ranging from 8 to 18, are generally added. By virtue of their amphiphilic structure, these emulsifiers position themselves at the oil phase/aqueous phase interface, and thus stabilize the dispersed oil droplets. Despite the presence of emulsifiers, the emulsions may have a tendency to become destabilized. Coalescence and then separation of the aqueous and oily phases with release of oil then takes place. To improve the stability of these nanoemulsions, the concentration of emulsifiers may be increased, but, at high concentrations, they lead to a coarse, sticky or tacky feel and also to problems of harmlessness with respect to the skin, the eyes or mucous membranes.

To solve the stability problems of standard direct emulsions, it was proposed to prepare direct emulsions obtained via the phase inversion temperature technique (PIT emulsions). These PIT emulsions, also known as nanoemulsions, have a mean size of the globules constituting the lipophilic phase that is within determined limits, i.e. less than a nanometer. The principle of emulsification via the phase inversion temperature (PIT) technique is, in its principle, well known to those skilled in the art. It was described in 1968 by K. Shinoda (J. Chem. Soc. Jpn, 1968, 89, 435). It was shown that this technique makes it possible to obtain fine, stable emulsions (K. Shinoda et H. Saito, J. Colloid Interface Sci., 1969, 30, 258). This technology was applied in cosmetics as early as 1972 by Mitsui et al. ("Application of the phase-inversion-temperature method to the emulsification of cosmetics"; T. Mitsui, Y. Machida and F. Harusawa, American, Cosmet. Perfum., 1972, 87, 33).

Moreover, it is advantageous to have available fine emulsions, i.e. emulsions in which the lipophilic phase is in the form of nanodroplets, i.e. droplets less than a nanometer in size, since these very fine emulsions are generally more stable than the direct emulsions obtained mechanically. These emulsions, also known as nanoemulsions, have blueish tints and Newtonian behavior. These nanoemulsions are very widely used for vaporizable products, in varied fields such as care, antiperspirants, suncare or, especially, in wipes.

The principle of this technique is as follows: a mixture of an aqueous phase and a lipophilic phase is prepared, and is brought to a temperature above the PIT temperature, the phase inversion temperature of the system, which is the temperature at which the equilibrium between the hydrophilic and lipophilic properties of the emulsifier(s) used is reached. At high temperature, i.e. above the phase inversion temperature ($>T_{PIT}$), the emulsion is of water-in-oil type. During its cooling, it passes through a state of microemulsion or nanoemulsion. The water-in-oil emulsion thus becomes inverted at the phase inversion temperature, to become an emulsion of oil-in-water type. The advantage of the process is that it provides finer emulsions than standard emulsions.

The lipophilic phases, also known as the fatty phases or oily phases, of these nanoemulsions are generally constituted of linear alkanes (for example nonane, dodecane or tetradecane), mineral oils or isoparaffins. In the case of linear alkanes, the formation the nanoemulsion is influenced by the length of the carbon chain: the shorter the carbon chain, the more the PIT temperature decreases. However, the formulations are limited since, for a number of carbons of less than 12 (C<12), the n-alkanes are irritant and thus sparingly used in cosmetics. And above 14 carbons (C>14), the pour point (PP) is greater than 5° C., and the emulsions therefore cannot be used "cold" or are not vaporizable. ("The effect of combination of various oils, emulsifiers and additives on the phase inversion temperature in emulsion systems" Bulletin of the Chemical Society of Japan (1970), 43(10), 3044-8, Mitsui, Takeo; Machida, Yasuhiko; Harusawa, Fuminori; "Assessment of skin irritation and molecular responses in rat skin exposed to nonane, dodecane, tetradecane", R. J. Babu, 2004). Mineral oils (paraffinum liquidum in cosmetics) are used for this type of composition, but their high viscosity gives rise to high PIT temperatures and thus substantial energy consumption during the preparation of the emulsions. Furthermore, mineral oils are known to be occlusive to the skin and irritant if they are not sufficiently pure. Nanoemulsions comprising only isoparaffins as fatty phase are unstable. Specifically, the degree of branching of the molecules destabilizes the emulsion. For example, isohexadecane, which is very widely used in cosmetics, cannot be used alone to formulate PIT emulsions on account of the low stability of the emulsions obtained. Furthermore, for C<12 and at high concentrations, which is the case for nanoemulsions with fatty phase concentrations of about 20%, isoparaffins are irritant since they penetrate into the skin. ("Formation and stability of nano-emulsions" Advances in Colloid and Interface Science (2004), 108-109, 303-318, Tadros, Tharwat; Izquierdo, P.; Esquena, J.; Solans, C.). WO 02/032390 A1 describes fragrancing compositions in oil-in-water nanoemulsion form. The examples in said document use polyethoxylated nonionic surfactants which belong to the following families: polyethylene glycol stearyl ethers (Brij® 78P and Brij® 721) and polyethylene glycol oleyl ethers (Brij® 98V).

Finally, the problem of the stability of PIT emulsions due to certain fatty phases may possibly be overcome by using a large amount of emulsifying system relative to the amount of lipophilic phase. However, this then results in a composition which has relatively unsatisfactory cosmetic qualities, especially in terms of feel, skincare, especially skin protection against dehydration.

There is thus still a need to improve the intrinsic characteristics of these PIT nanoemulsions.

The Applicant has found, surprisingly, that the choice of particular compounds in the lipophilic phase makes it possible to produce stable and non-irritant PIT nanoemulsions with a low phase inversion temperature.

The Applicant has discovered, surprisingly, that the choice of a particular emulsifying system makes it possible to produce stable, non-irritant PIT nanoemulsions with a low phase inversion temperature and with a large amount of lipophilic phase.

The object of the present invention is to provide a cosmetic or dermatological composition obtained at a low phase inversion temperature.

The object of the invention is also to propose a stable cosmetic or dermatological composition.

SUMMARY OF THE INVENTION

These objects are achieved by means of a novel cosmetic or dermatological composition.

The invention relates to a cosmetic or dermatological composition in the form of an oil-in-water nanoemulsion comprising:
- a lipophilic phase (a) which comprises at least one hydrocarbon-based oil comprising at least one isoparaffin, and at least one cycloalkane,
- an emulsifying system (b) comprising at least one nonionic emulsifier,
- an aqueous phase (c),
- the lipophilic phase (a)/emulsifying system (b) weight ratio being greater than or equal to 0.5.

Preferably, the emulsifying system of the composition according to the invention is composed of at least 95%, more preferentially at least 98% or even at least 99% by weight of emulsifiers chosen from adducts of ethylene oxide with cetearyl or cetylstearyl alcohol comprising from 10 to 20 oxyethylene groups, glyceryl stearate and cetearyl alcohol, relative to the total weight of the emulsifying system. Preferably, the emulsifying system of the composition according to the invention is constituted of Ceteareth-20, Ceteareth-12, cetearyl alcohol and glyceryl stearate.

Preferably, the composition of the invention comprises an amount of lipophilic phase (a) ranging from 5% to 40%, preferentially from 10% to 35%, more preferentially from 15% to 30% and even more preferentially from 20% to 30% by weight relative to the total weight of the composition.

Preferably, the lipophilic phase (a) of the composition of the invention comprises from 15% to 100% by weight of hydrocarbon-based oil, preferentially from 20% to 90%, more preferentially from 25% to 80% and even more preferentially between 30% to 70% by weight of hydrocarbon-based oil relative to the total weight of the lipophilic phase.

Preferably, the hydrocarbon-based oil of the lipophilic phase (a) of the composition of the invention is a hydrogenated hydrocarbon-based oil.

Preferably, the hydrocarbon-based oil of the lipophilic phase (a) of the composition of the invention is chosen from isoparaffins, normal paraffins and/or cycloalkanes comprising 12 to 29 carbon atoms, preferentially 13 to 23 carbon atoms and more preferentially 18 to 21 carbon atoms.

Preferably, the hydrocarbon-based oil of the lipophilic phase (a) of the composition of the invention has a content of paraffinic compounds ranging from 40% to 99%, preferentially from 45% to 90% and more preferentially from 60% to 80%.

Preferably, the hydrocarbon-based oil of the lipophilic phase (a) of the composition of the invention has a content of naphthenic compounds ranging from 1% to 60%, preferentially from 10% to 55% and more preferentially from 20% to 40%.

Preferably, the hydrocarbon-based oil of the lipophilic phase (a) of the composition of the invention has a content of isoparaffins ranging from 30% to 90%, preferably from 40% to 80% and more preferentially from 50% to 70%.

Preferably, the hydrocarbon-based oil of the lipophilic phase (a) of the composition of the invention has a content of normal paraffins ranging from 0.01% to 30%, preferably from 0.01% to 25% and more preferentially from 5% to 20%.

Advantageously, the hydrocarbon-based oil of the lipophilic phase (a) of the composition of the invention comprises from 30% to 90% of isoparaffins, from 0.01% to 30% of normal paraffins and from 1% to 60% of naphthenic compounds.

Preferably, the composition of the invention comprises an amount of emulsifying system (b) ranging from 2% to 15%, preferentially from 3% to 14%, more preferentially from 4% to 12% and even more preferentially from 5% to 11% by weight relative to the total weight of the composition.

Advantageously, the emulsifying system (b) of the composition of the invention comprises at least one lipophilic emulsifier and one hydrophilic emulsifier.

According to one embodiment, the composition of the invention is obtained via the phase inversion temperature technique.

Another subject of the invention is the cosmetic use of the composition of the invention for a topical application. The invention in particular concerns the use of said composition as a suncare product, as a skincare product or as a makeup product.

Another subject of the invention is also the use of the composition of the invention for the formulation of cosmetic products or dermatological products.

DETAILED DESCRIPTION OF THE INVENTION

The invention relates to a cosmetic or dermatological composition in the form of an oil-in-water nanoemulsion comprising a lipophilic phase which comprises at least one hydrocarbon-based oil comprising at least one isoparaffin and at least one cycloalkane, optionally at least one normal paraffin, an emulsifying system comprising at least one nonionic emulsifier and an aqueous phase with a lipophilic phase/emulsifying system ratio of greater than or equal to 0.5 by weight.

The invention in particular relates to a composition comprising an oil-in-water (O/W) nanoemulsion obtained via the phase inversion temperature (PIT) technique.

The composition according to the invention in particular comprises an O/W nanoemulsion for obtaining a stable composition.

The composition according to the invention in particular comprises an O/W nanoemulsion allowing phase inversion at a low temperature.

The composition according to the invention in particular comprises an O/W nanoemulsion whose lipophilic phase is non-irritant, non-occlusive and biodegradable.

Lipophilic Phase:

The composition according to the invention preferably comprises an amount of lipophilic phase, also known as fatty phase or oily phase, ranging from 5% to 40%, preferentially from 10% to 35%, more preferentially from 15% to 30% and even more preferentially from 20% to 30% by weight relative to the total weight of the composition.

The presence of a significant amount of lipophilic phase contributes toward the cosmetic qualities of the composition: pleasant feel, care and protection of the skin, especially against dehydration.

The lipophilic phase of the composition according to the invention comprises at least one hydrocarbon-based oil. The hydrocarbon-based oil preferably has a content of paraffinic compounds ranging from 40% to 99%, preferentially from 45% to 90% and more preferentially from 60% to 80%. As a general rule, these paraffins are mixtures.

The hydrocarbon-based oil advantageously comprises a mixture of isoparaffins and of normal paraffins. Preferably, the content of isoparaffins in the hydrocarbon-based oil is from 30% to 90%, preferentially from 40% to 80% and more preferentially from 50% to 70%. Preferably, the content of normal paraffins in the hydrocarbon-based oil is from 0.01% to 30%, preferentially from 0.01% to 25% and more preferentially from 5% to 20%.

The hydrocarbon-based oil also preferably has a content of naphthenic compounds, also known as cycloalkanes, ranging from 1% to 60%, preferentially from 10% to 55% and more preferentially from 20% to 40%.

According to a preferred embodiment, the hydrocarbon-based oil comprises from 30% to 90% of isoparaffins, from 0.01% to 30% of normal paraffins and from 1% to 60% of cycloalkanes. Preferably, the hydrocarbon-based oil comprises from 40% to 80% of isoparaffins, from 0.01% to 25% of normal paraffins and from 10% to 55% of cycloalkanes. More preferably, the hydrocarbon-based oil comprises from 50% to 70% of isoparaffins, from 5% to 20% of normal paraffins and from 20% to 40% of cycloalkanes.

The hydrocarbon-based oil used in the composition according to the invention is advantageously free of aromatic compounds. The term "free of" means a content of aromatic compounds of less than 500 ppm, preferably less than 300 ppm and more preferentially less than 150 ppm measured by UV spectrometry.

The hydrocarbon-based oil also preferably has a kinematic viscosity at 40° C. ranging from 1 to 12 cSt, preferentially from 2 to 8 cSt and more preferentially from 3 to 7 cSt according to standard ASTM D445.

The hydrocarbon-based oil preferably has a typical pour point according to standard ASTM D97 ranging from 10 to −60° C., preferentially from 5 to −50° C. and more preferentially from 0 to −20° C.

Such hydrocarbon-based oil compositions may be obtained in the following manner. The hydrocarbon-based oil according to the invention is a hydrocarbon fraction that may be derived in a known manner from crude oil or from biomass.

Preferably, for the purposes of the invention, the term "hydrocarbon fraction" means a fraction derived from the distillation of crude oil, preferably derived from the atmospheric distillation and/or vacuum distillation of crude oil, preferably derived from atmospheric distillation followed by vacuum distillation.

The hydrocarbon fraction used in the cosmetic or dermatological composition of the invention is advantageously obtained via a process comprising hydrotreatment, hydrocracking or catalytic cracking steps.

The hydrocarbon fraction used in the cosmetic or dermatological composition of the invention is preferably obtained via a process comprising steps of dearomatization and optionally desulfurization.

Preferably, the hydrocarbon fraction obtained after the distillation step(s) is a gas oil fraction. This gas oil fraction is preferably obtained via a process comprising hydrotreatment, hydrocracking, catalytic cracking steps, optionally followed by dearomatization and optionally desulfurization steps.

The hydrocarbon fraction may be a mixture of hydrocarbon fractions that has undergone the steps described above.

The hydrocarbon fraction used in the composition of the invention may also be derived from the conversion of biomass.

The term "derived from the conversion of biomass" refers to a hydrocarbon fraction produced from raw materials of biological origin preferably chosen from plant oils, animal fats, fish oils and mixtures thereof. The suitable raw materials of biological origin are, for example, rapeseed oil, canola oil, tall oil, sunflower oil, soybean oil, flax oil, olive oil, linseed oil, mustard oil, palm oil, groundnut oil, castor oil, coconut oil, animal fats such as tallow, recycled food fats, raw materials derived from genetic engineering, and biological raw materials produced from microorganisms such as algae and bacteria.

Preferably, the hydrocarbon fraction of biological origin is obtained via a process comprising hydrodeoxygenation (HDO) and isomerization steps. The hydrodeoxygenation (HDO) step leads to the decomposition of the biological ester structures or of the triglyceride constituents, to the removal of the oxygen-based, phosphorus-based and sulfur-based compounds and to the hydrogenation of the olefinic bonds. The product derived from the hydrodeoxygenation reaction is then isomerized. A fractionation step may preferably follow the hydrodeoxygenation and isomerization steps.

The fractions of interest are then subjected to hydrotreatment and then distillation steps so as to obtain the specifications for the hydrocarbon fraction desired according to the invention.

The hydrocarbon fraction may be a mixture of hydrocarbon fractions derived from the distillation of crude oil and/or from the conversion of biomass.

The hydrocarbon-based oil used in the composition of the invention is advantageously a hydrocarbon fraction with a distillation range DR (in ° C.) ranging from 220° C. to 380° C., preferably from 220° C. to 370° C. and even more preferentially from 240° C. to 335° C. measured according to standard ASTM D86. Preferably, the difference between the initial boiling point and the final boiling point is less than or equal to 150° C. The hydrocarbon-based oil may comprise one or more fractions with distillation ranges within the ranges described above.

Advantageously, the hydrocarbon-based oil used in the cosmetic or dermatological composition of the invention is totally saturated. Preferably, the components of the hydrocarbon-based oil are chosen from isoparaffins, normal paraffins and cycloalkanes comprising 12 to 29 carbon atoms, preferentially 13 to 23 carbon atoms and more preferentially 18 to 21 carbon atoms.

Advantageously, said lipophilic phase of the cosmetic or dermatological composition according to the invention comprises from 15% to 100% by weight of at least one hydrocarbon-based oil as described above, preferentially from 20% to 90%, more preferentially from 25% to 80% and even more preferentially 30% to 70% by weight relative to the total weight of the lipophilic phase.

The lipophilic phase may also contain up to 85% by weight, relative to the total weight of the lipophilic phase, of one or more other oils chosen from fatty acid esters, ethers, plant oils, silicone oils, fluoro oils, which may be volatile or nonvolatile. Oils of this type that may especially be mentioned include:

esters, such as 2-ethylhexyl caprate/caprylate (or octyl caprate/caprylate), ethyl laurate, butyl laurate, hexyl laurate, isohexyl laurate, isopropyl laurate, methyl myristate, ethyl myristate, butyl myristate, isobutyl myristate, isopropyl myristate, 2-ethylhexyl monococoate (or octyl monococoate), methyl palmitate, ethyl palmitate, isopropyl palmitate, isobutyl palmitate, butyl stearate, isopropyl stearate, isobutyl stearate, isopropyl isostearate, 2-ethylhexyl pelargonate (or octyl pelargonate), 2-ethylhexyl hydroxystearate (or octyl hydroxystearate), decyl oleate, diisopropyl adipate, bis(2-ethylhexyl) adipate (or dioctyl adipate), diisocetyl adipate, 2-ethylhexyl succinate (or octyl succinate), diisopropyl sebacate, 2-ethylhexyl malate (or octyl malate), pentaerythritol caprate/caprylate, 2-ethylhexyl hexanoate (or octyl hexanoate), octyldodecyl octanoate, isodecyl neopentanoate, isostearyl neopentanoate, isononyl isononanoate, isotridecyl isononanoate, lauryl lactate, myristyl lactate, cetyl lactate, myristyl propionate, 2-ethylhexyl 2-ethylhexanoate (or octyl 2-ethylhexanoate), 2-ethylhexyl octanoate (or octyl octanoate), isopropyl lauroyl sarcosinate (Eldew SL 205 from Unipex), dicaprylyl carbonate (Cetiol CC from Cognis), and mixtures thereof;

ethers such as dicaprylyl ether (Cetiol OE from Cognis);

hydrocarbon-based oils of plant origin such as sweet almond oil, avocado oil, castor oil, coriander oil, olive oil, jojoba oil, sesame oil, groundnut oil, grapeseed oil, rapeseed oil, coconut oil, hazelnut oil, shea butter, palm oil, apricot kernel oil, beauty-leaf oil, rice bran oil, corn germ oil, wheat germ oil, soybean oil, sunflower oil, evening primrose oil, safflower oil, passionflower oil, rye oil, caprylic/capric acid triglycerides such as those sold by the company Stéarineries Dubois or those sold under the names Miglyol 810, 812 and 818 by the company Dynamit Nobel;

volatile or nonvolatile silicone oils, such as volatile or nonvolatile polydimethylsiloxanes (PDMS) bearing a linear or cyclic silicone chain, which are liquid or pasty at room temperature, especially cyclopolydimethylsiloxanes (cyclomethicones) such as cyclohexasiloxane; polydimethylsiloxanes comprising alkyl, alkoxy or phenyl groups, on the side or at the end of the silicone chain, these groups containing from 2 to 24 carbon atoms; phenyl silicones such as phenyl trimethicones, phenyl dimethicones, phenyltrimethylsiloxydiphenylsiloxanes, diphenyl dimethicones, diphenylmethyldiphenyltrisiloxanes, 2-phenylethyl trimethylsiloxysilicates, polymethylphenylsiloxanes;

fluoro oils such as partially hydrocarbon-based and/or silicone-based fluoro oils such as those described in JP-A-2-295 912.

The other lipophilic constituents that may be present in the lipophilic phase are, for example, waxes; gums such as silicone gums (dimethiconol); silicone resins such as trifluoromethyl-C1-4-alkyldimethicone and trifluoropropyl dimethicone; pastes such as petrolatum; and mixtures thereof.

Emulsifying System:

Nonionic emulsifying systems comprising at least one hydrophilic emulsifier and at least one lipophilic emulsifier make it possible to produce emulsions via the phase inversion temperature technique, known as PIT emulsions, which are reputed for being very stable. The calculation of phase inversion in concentrated emulsions (CAPICO) is possible from the EACN (equivalent alkane carbon number) values and gives a proportion of emulsifiers and of fatty phase corresponding to a given phase inversion temperature (PIT). In addition, CAPICO is a calculation method for determining the dose of emulsifier required to emulsify a given fatty phase (constructed relative to the sensory and chemical characteristics) (International Journal of Cosmetic Science 1994 April; 16(2): 84-92 "Calculation of optimum emulsifier mixtures for phase inversion emulsification" Forster T., Rybinski W. V., Tesmann H., Wadle A. (Henkel KGaA)).

Emulsifiers have the particular feature of facilitating the dispersion of two phases that are mutually insoluble. The HLB (hydrophilic-lipophilic balance) is the ratio between the hydrophilic part and the lipophilic part in their molecule. This term HLB is well known to those skilled in the art and is described in "The HLB system. A time-saving guide to emulsifier selection" (published by ICI Americas Inc.; 1984).

The emulsifying system used in the composition according to the invention comprises one or more nonionic emulsifiers. Preferably, it comprises at least one hydrophilic emulsifier and at least one lipophilic emulsifier.

Preferably, these nonionic emulsifiers are oxyethylenated and/or glycerolated emulsifiers with an HLB ranging from 8 to 18 and preferably from 10 to 16.

The emulsifying system may comprise, in particular, one or more oxyethylenated and/or glycerolated nonionic emulsifiers chosen from ethoxylated fatty alcohols, fatty acid esters of PEG, partial glycerides of ethoxylated fatty acids, polyglycerolated fatty acid triglycerides and ethoxylated derivatives thereof.

The ethoxylated fatty alcohols are preferably chosen from C18 to C22 fatty alcohols containing from 6 to 12 and preferably from 8 to 12 mol of ethylene oxide. Examples of ethoxylated fatty alcohols that may especially be mentioned include adducts of ethylene oxide with behenyl alcohol, especially those comprising from 6 to 12 oxyethylene groups (for example Beheneth-9 or Beheneth-10 according to the CTFA name); adducts of ethylene oxide with stearyl alcohol, especially those comprising from 2 to 21 oxyethylene groups (for example Steareth-9 according to the CTFA name); adducts of ethylene oxide with isostearyl alcohol, especially those comprising from 6 to 12 oxyethylene groups (Isosteareth-9 according to the CTFA name); and mixtures thereof.

As oxyethylenated and/or glycerolated nonionic emulsifiers with an HLB ranging from 8 to 18, the composition may also comprise oxyethylenated fatty alcohols other than those described above, namely adducts of ethylene oxide with lauryl alcohol, especially those comprising from 9 to 50 oxyethylene groups (Laureth-9 to Laureth-50 according to the CTFA name); adducts of ethylene oxide with cetearyl alcohol or cetylstearyl alcohol (mixture of cetyl alcohol and stearyl alcohol), especially those comprising from 9 to 30 oxyethylene groups (Ceteareth-9 to Ceteareth-30 according to the CTFA name); adducts of ethylene oxide with cetyl alcohol, especially those comprising from 9 to 30 oxyethylene groups (Ceteth-9 to Ceteth-30 according to the CTFA name); and mixtures thereof.

The fatty acid esters of PEG are preferably chosen from the compounds of formula (I) below:

$$R—COO—(CH_2—CH_2—O)_mH \quad (I)$$

in which R is a linear or branched, saturated or unsaturated hydrocarbon-based chain containing from 10 to 24 carbon atoms, and m is an integer ranging from 8 to 50.

Examples of fatty acid esters of PEG that may be mentioned include products of esterification with lauric, palmitic, stearic or behenic acids, and mixtures thereof and with ethylene oxide, especially those comprising from 9 to 50 oxyethylene groups such as PEG-9 to PEG-50 laurates (according to the CTFA name: PEG-9 laurate to PEG-50 laurate); PEG-9 to PEG-50 palmitates (according to the CTFA name: PEG-9 palmitate to PEG-50 palmitate); PEG-9 to PEG-50 stearate (according to the CTFA name: PEG-9 stearate to PEG-50 stearate); PEG-9 to PEG-50 palmitostearates; PEG-9 to PEG-50 behenates (according to the CTFA name: PEG-9 behenate to PEG-50 behenate); and mixtures thereof.

The cosmetic or dermatological composition may also comprise additional emulsifiers. As additional emulsifiers, use may be made of fatty acid salts containing 8 to 30 carbon atoms, for instance palmitic acid, stearic acid or behenic acid salts; fatty esters of glycerol, for instance glyceryl stearate; oxyethylenated derivatives of salts of fatty acids and of fatty esters of glycerol, comprising 2 to 8 ethylene oxide groups, and mixtures thereof.

Preferably, the oxyethylenated and/or glycerolated nonionic emulsifiers with an HLB ranging from 8 to 18 are chosen from adducts of ethylene oxide with cetearyl alcohol or cetylstearyl alcohol (mixture of cetyl alcohol and stearyl alcohol), especially those comprising from 9 to 30 oxyethylene groups, esters of glycerol and of stearic acid and cetearyl alcohol.

Even more preferentially, the emulsifying system of the composition according to the invention is composed of at least 95%, more preferentially at least 98% or even at least 99% by weight of emulsifiers chosen from adducts of ethylene oxide with cetearyl or cetylstearyl alcohol comprising from 10 to 20 oxyethylene groups, glyceryl stearate and cetearyl alcohol, relative to the total weight of the emulsifying system.

Ideally, the emulsifying system of the composition according to the invention is preferably constituted of Ceteareth-20, Ceteareth-12, cetearyl alcohol and glyceryl stearate.

In general, the oxyethylenated and/or glycerolated nonionic surfactant(s) with an HLB ranging from 8 to 18 are preferably present in an amount ranging from 2 to 15%, preferentially from 3% to 14%, more preferentially from 4% to 12% and even more preferentially from 5% to 11% by weight relative to the total weight of the composition.

Aqueous Phase:

The cosmetic or dermatological composition according to the invention comprises an amount of aqueous phase of greater than or equal to 50% by weight relative to the total weight of the composition, preferably greater than or equal to 55% and more preferentially greater than or equal to 60%.

According to one embodiment of the invention, the composition of the invention comprises at least one polyol (or polyhydric alcohol) which is generally present in the aqueous phase. Examples of polyols that may be mentioned include glycerol; glycols such as propylene glycol, butylene glycol, isopropylene glycol and polyethylene glycols such as PEG-8; sorbitol; sugars such as glucose, fructose, maltose, lactose or sucrose; and mixtures thereof.

The amount of polyols generally ranges from 0.1% to 60% by weight and better still from 0.5% to 50% by weight relative to the total weight of the aqueous phase. Conventionally, the aqueous phase may comprise, besides water and the polyol(s), one or more water-soluble solvents chosen from water-soluble lower alcohols. The term "lower alcohol" means an alcohol comprising from 1 to 8 carbon atoms. Examples of lower alcohols that may be mentioned include ethanol, isopropanol and butanol, and mixtures thereof. When they are present in the composition of the invention, the water-soluble lower alcohol(s) may be in an amount ranging from 0.01% to 40% by weight and preferably from 0.01% to 20% by weight relative to the total weight of the aqueous phase.

Additives:

The cosmetic or dermatological composition according to the invention may also contain any adjuvant or additive usually used in the fields under consideration and especially in the cosmetic or dermatological fields. Needless to say, a person skilled in the art will take care to choose the optional additive(s) of the composition according to the invention so that the advantageous properties intrinsically associated with the composition in accordance with the invention are not, or are not substantially, impaired by the envisaged addition.

Among the conventional adjuvants that may be contained in the aqueous phase and/or in the oily phase of the nanoemulsions in accordance with the invention (depending on the water-soluble or liposoluble nature of these adjuvants), mention may be made especially of anionic foaming surfactants (such as sodium lauryl ether sulfate, sodium alkyl phosphate, sodium trideceth sulfate), amphoteric foaming surfactants (such as alkyl betaine, disodium cocoamphodiacetate) or nonionic foaming surfactants with an HLB of greater than 10 (such as POE/PPG/POE, alkylpolyglucoside, polyglyceryl-3 hydroxylauryl ether); preserving agents; sequestrants (EDTA); antioxidants; fragrances; dyestuffs such as soluble dyes, pigments and nacres; matt-effect, tensioning, whitening or exfoliant fillers; sunscreens; cosmetic or dermatological active agents and hydrophilic or lipophilic agents having the effect of improving the cosmetic properties of the skin; electrolytes; hydrophilic or lipophilic, anionic, nonionic, cationic or amphoteric polymers, thickeners, gelling agents or dispersants. The amounts of these various adjuvants are those conventionally used in the field under consideration, for example from 0.01 to 20% of the total weight of the composition.

As active agents that may be used in the cosmetic or dermatological composition of the invention, examples that may be mentioned include water-soluble or liposoluble vitamins such as vitamin A (retinol), vitamin E (tocopherol), vitamin C (ascorbic acid), vitamin B5 (panthenol), vitamin B3 (niacinamide), derivatives of these vitamins (especially esters) and mixtures thereof; antiseptics; antibacterial active agents such as 2,4,4'-trichloro-2'-hydroxydiphenyl ether (or Triclosan), 3,4,4'-trichlorocarbanilide (or Triclocarban); antiseborrheic agents; antimicrobial agents such as benzoyl peroxide or niacin (vitamin PP); slimming agents such as caffeine; optical brighteners, and any active agent that is suitable for the final purpose of the composition, and mixtures thereof.

The amount of active agents depends on the desired aim. The active agent(s) may be present, for example, in a concentration ranging from 0.001% to 20%, preferably from 0.01% to 10% and better still from 0.05% to 5% by weight relative to the total weight of the composition. These amounts are calculated in addition to the amounts of oily, emulsifying and aqueous phases detailed above.

Preparation Process:

The cosmetic or dermatological composition according to the invention is a nanoemulsion obtained via the phase inversion temperature technique fully described in the prior art. This preparation process comprises at least the steps consisting in:

weighing out all the constituents of the composition (with the exception of the heat-sensitive starting materials),
mixing the lipophilic phase with the emulsifying system, gradually and separately heating the aqueous phase and the lipophilic phase supplemented with the emulsifying system up to a temperature T, mixing and homogenizing the aqueous phase and the lipophilic phase supplemented with the emulsifying system, heating the mixture formed with moderate stirring at a temperature T1 above or equal to the phase inversion temperature (PIT temperature), abruptly cooling with gentle stirring at 100 rpm, when the temperature has fallen below the phase inversion zone, optionally adding the heat-sensitive starting materials.

During the initial mixing, the emulsion is an oil-in-water emulsion. When heating is continued, the emulsion inverts at the PIT temperature. A water-in-oil emulsion is thus obtained. On cooling, the emulsion inverts again and once again becomes an oil-in-water emulsion on passing through the PIT temperature. The cooling rate will determine the size of the droplets. It is preferable for the cooling to be abrupt and with gentle stirring.

When the PIT temperature is reached, the mixture becomes transparent or more transparent. In the nanoemulsion formation zone (translucent mixture), the hydrophilic and hydrophobic interactions are equilibrated since the tendency of the emulsifying system is to form both direct micelles and reverse micelles.

PIT Composition:

The cosmetic or dermatological composition according to the invention advantageously comprises from 5% to 40% by weight of a lipophilic phase, from 2% to 15% by weight of an emulsifying system and at least 50% by weight of an aqueous phase as described above relative to the total weight of the composition.

Preferably, the composition according to the invention comprises from 10% to 35% by weight of a lipophilic phase and from 3% to 14% by weight of an emulsifying system, more preferentially from 15% to 30% by weight of a lipophilic phase and from 4% to 12% by weight of an emulsifying system, even more preferentially from 20% to 30% by weight of a lipophilic phase and from 5% to 11% by weight of an emulsifying system, and at least 50% by weight of an aqueous phase as described above relative to the total weight of the composition.

The lipophilic phase/emulsifying system weight ratio of the composition according to the invention is greater than or equal to 0.5, preferably greater than or equal to 1.5 and more preferentially greater than or equal to 2.5. Preferentially, the lipophilic phase/emulsifying system weight ratio of the composition according to the invention is from 0.5 to 4.

The cosmetic or dermatological composition according to the invention advantageously comprises from 5% to 40% by weight of a lipophilic phase, from 2% to 15% by weight of an emulsifying system and at least 50% by weight of an aqueous phase as described above relative to the total weight of the composition and the lipophilic phase/emulsifying system weight ratio of the composition is from 1 to 4.

Preferably, the composition according to the invention comprises from 10% to 35% by weight of a lipophilic phase, from 3% to 14% by weight of an emulsifying system and at least 50% by weight of an aqueous phase as described above relative to the total weight of the composition and the lipophilic phase/emulsifying system weight ratio of the composition is from 1.5 to 4.

Preferably, the mean size of the nanoemulsion droplets of the composition according to the invention ranges from 0.1 to 0.5 μm, which is a distinctive characteristic of the nanoemulsions.

The dynamic viscosity of the composition according to the invention is preferably less than or equal to 0.5 Pa·s at 25° C. measured using Brookfield apparatus.

The cosmetic or dermatological composition according to the invention is in the form of a more or less soft cream or of a vaporizable emulsion: it may constitute, for example, a cosmetic or dermatological composition such as a makeup-removing or cleansing composition for the skin or the lips, a suncare (UV protection) or aftersun composition, a skin massage composition, a shower care balm composition, an antiperspirant composition, a mask composition, a repairing balm composition, a scrubbing and/or exfoliant composition either for the face or for the hands (when it contains exfoliant particles), a makeup composition, a composition for wipes or a vaporizable composition.

The composition of the invention is advantageously characterized by the fact that it has stability whose duration is greater than or equal to 4 weeks, advantageously greater than or equal to 6 weeks, the stability being evaluated after storage without agitation at a temperature of 50° C. and corresponding to a visually evaluated resistance to phase separation.

Use of the PIT Composition:

A subject of the invention is also the cosmetic or dermatological use of the composition as defined above for a topical application.

A subject of the invention is also the cosmetic or dermatological use of the composition as defined above as a skincare product, as a hygiene product, as a suncare product or as a makeup product.

A subject of the invention is also a cosmetic or dermatological process for treating the skin, comprising the application to the skin of a composition as defined above.

The composition of the invention may also be used for the formulation of cosmetic compositions or dermatological compositions comprising components or phases other than those described above. It may especially concern the formulation of care, hygiene or makeup compositions.

EXAMPLES

In the rest of the present description, examples are given as illustrations of the present invention and are not in any way intended to limit the scope thereof.

Various nanoemulsion formulations based on hydrocarbon-based oils were evaluated.

The nanoemulsions according to the examples comprise an aqueous phase, a lipophilic phase comprising at least one hydrocarbon-based oil and an emulsifying system composed of nonionic oil-in-water (O/W) emulsifiers.

Emulsifying System:

Two nonionic O/W emulsifiers were selected. The emulsifiers Eumulgin B2 and Emulgade SEV sold by the company BASF are particularly indicated for emulsions formed via the phase inversion temperature technique. This concerns a system of nonionic emulsifiers, in which Eumulgin B2 is hydrophilic and Emulgade SEV is lipophilic.

The chemical structures of these two emulsifiers are indicated in table 1:

Eumulgin B2, INCI: Ceteareth-20,

Emulgade SEV, INCI: glyceryl stearate and Ceteareth-20 and Ceteareth-12 and cetearyl alcohol

TABLE 1

| Ceteareth-n in which 2 < n < 100 and m = 15 or 17 | Cetearyl alcohol (13 < n < 15) | Glyceryl stearate |
|---|---|---|
| $CH_3-(CH_2)_m-(O-CH_2-CH_2)_n-OH$ | $CH_3-(CH_2)_n-CH_2-OH$ | (structure shown) |

Lipophilic Phase:

The various lipophilic phases according to the examples comprise various hydrocarbon-based oils. The oils Gemseal 25®, Gemseal 60® and Gemseal 120® sold by the company Total Fluides are hydrocarbon-based oils according to the invention. Oil 4 is a comparative example of a hydrocarbon-based oil frequently encountered in the prior art, isohexadecane.

Table 2 indicates the physicochemical characteristics of each of the hydrocarbon-based oils according to the examples.

TABLE 2

| Parameters | Gemseal 25 ® | Gemseal 60 ® | Gemseal 120 ® | Oil 4 |
|---|---|---|---|---|
| Carbon distribution | C13-15 alkane | C18-21 alkane | C21-28 alkane | C16 alkane |
| Distillation range (° C.) [ASTM D86] | 220-275 | 220-270 | 330-380 | 210-250 |
| Pour point (° C.) [ASTM D97] | −50 | −0.5 | −30 | −70 |
| Viscosity at 40° C. (cSt) [ASTM D445] | 2.5 | 6 | 11 | 3 |
| Aromatics (%) [spectrometry UV] | <0.03 | <0.03 | <0.03 | — |
| Mono-aromatics (ppm) [spectrometry UV] | 6.5 | 103 | 57 | — |
| Paraffins (%) [GC2D] | 45 | 68 | 46 | 100 |
| Isoparaffins (%) [GC2D] | <40 | <60 | <50 | 100 |
| n-Paraffins (%) [GC2D] | >5 | >8 | >0.01 | 0 |
| Naphthenes (%) [GC2D] | 54.7 | 31.8 | 53.8 | 0 |

These oils Gemseal 25®, Gemseal 60® and Gemseal 120® are known to be non-irritant, non-occlusive and biodegradable and are thus compatible with cosmetic use.

As a result, the lipophilic phases of the nanoemulsions formulated with the oils Gemseal 25®, Gemseal 60® and Gemseal 120® are nontoxic, non-irritant, non-comedogenic and biodegradable.

The total amount of lipophilic phase remains fixed at 25% by weight relative to the total weight of the nanoemulsion and the amount of hydrocarbon-based oil included in this lipophilic phase is 20% by weight relative to the total weight of the nanoemulsion. The remaining 5% are compensated for in each formulation by a standard ester, which is more polar than the paraffinic hydrocarbon-based oil, isononyl isononanoate or ININ, which is very frequently found in emulsions. 25% of lipophilic phase represents the amount of lipophilic phase of a product for mature skin, and is thus a significant amount.

Aqueous Phase:

The aqueous phase is predominantly composed of demineralized water. A preserving agent is incorporated to ensure the microbiological stability of the formulations and xanthan gum is added to help stabilize the aqueous phase of the formulation.

Formulation of the Nanoemulsions:

A nanoemulsion is formulated for each hydrocarbon-based oil, and thus four nanoemulsions in total are evaluated and compared. The percentages of emulsifiers tested are those given in table 1. They are the doses determined with the aid of the doses recommended by the suppliers of these emulsifiers and of the CAPICO system.

Table 3 below indicates the formulations of the four nanoemulsions according to the examples. The percentages indicated correspond to the weight of active material relative to the total weight of the composition.

TABLE 3

| | | Nano-emulsion 1 | Nano-emulsion 2 | Nano-emulsion 3 | Nano-emulsion 4 |
|---|---|---|---|---|---|
| Emulsifying system | Eumulgin B2 ® + Emulgade SEV ® | 2.2% + 7.8% | 2.2% + 7.8% | 2.2% + 7.8% | 2.2% + 7.8% |
| Lipophilic phase | Gemseal 25 ® | 20.00% | — | — | — |
| | Gemseal 60 ® | — | 20.00% | — | — |
| | Gemseal 120 ® | — | — | 20.00% | — |
| | Oil 4 | — | — | — | 20.00% |
| | Ester (isononyl isononanoate) | 5.00% | 5.00% | 5.00% | 5.00% |
| Aqueous phase | Demineralized water | qs | qs | qs | qs |
| | Xanthan gum | 0.20% | 0.20% | 0.20% | 0.20% |
| | Preserving agent | 0.50% | 0.50% | 0.50% | 0.50% |

The aqueous and lipophilic phases are heated to 60-65° C. separately, and the lipophilic phase is then poured into the aqueous phase; the emulsion thus formed is heated to 80° C.

with moderate stirring, and then cooled abruptly without stirring.

Results:

300 g of nanoemulsions are formulated for each of the results. Each of the nanoemulsions is then packaged in a 200 g jar and in a 30 g jar.

Phase inversion temperature:

The PIT temperature is measured at the time of formulation of each nanoemulsion.

Table 4 collates the PIT temperature measurements for each of the four nanoemulsions.

TABLE 4

|  | Nano-emulsion 1 | Nano-emulsion 2 | Nano-emulsion 3 | Nano-emulsion 4 |
|---|---|---|---|---|
| Hydrocarbon-based oil | Gemseal 25 ® | Gemseal 60 ® | Gemseal 120 ® | Oil 4 |
| PIT temperature (in ° C.) | 53 | 57 | 62 | 55 |

For each of the formulations of the nanoemulsions 1 to 3 according to the examples, low PIT temperatures that are industrially interesting are obtained. These very low phase inversion temperatures make it possible to avoid the problems associated with substantial heating: denaturing of the compounds, energy expenditure.

Stability:

The stability of the nanoemulsions according to the examples is evaluated visually at a temperature of 50° C. This observation after 1 week and 4 weeks makes it possible to see whether any phase separation of the composition of each nanoemulsion has taken place.

Table 5 indicates whether or not any separation of the various constituent phases of each nanoemulsion has been observed.

TABLE 5

|  |  | Nano-emulsion 1 | Nano-emulsion 2 | Nano-emulsion 3 | Nano-emulsion 4 |
|---|---|---|---|---|---|
|  | Hydrocarbon-based oil | Gemseal 25 ® | Gemseal 60 ® | Gemseal 120 ® | Oil 4 |
| Phase separation | 1 week | No | No | No | Yes |
|  | 4 weeks | No | No | No | Yes |

The results of the various stability tests demonstrate that the nanoemulsions 1 to 3 are entirely stable over time, unlike the nanoemulsion 4, for which phase separation of the composition is observed from the first week.

The various formulations of nanoemulsions 1, 2 and 3 according to the invention did not reveal any incompatibility between the illustrated hydrocarbon-based oils and the PIT system. On the contrary, these hydrocarbon-based oils make it possible to obtain, as demonstrated by the various results, nanoemulsions that are stable, sparingly viscous, non-irritant and non-occlusive with a low PIT temperature.

The invention claimed is:

1. A cosmetic or dermatological composition in the form of an oil-in-water nanoemulsion, comprising:
   a lipophilic phase (a) which comprises from 15% to 100% by weight, relative to the total weight of the lipophilic phase, of at least one hydrocarbon-based oil,
   from 3% to 14% by weight, relative to a total weight of the composition, of an emulsifying system (b), and
   at least 50% by weight, relative to a total weight of the composition, of an aqueous phase (c);
   wherein the cosmetic or dermatological composition in the form of an oil-in-water nanoemulsion is prepared by the phase inversion temperature (PIT) technique,
   wherein the at least one hydrocarbon-based oil of lipophilic phase (a) consists of paraffinic compounds and naphthenic compounds,
   wherein at least 95% by weight of the emulsifying system (b) is constituted of non-ionic emulsifiers selected from the group consisting of (i) adducts of ethylene oxide with cetearyl alcohol comprising from 10 to 20 oxyethylene groups, (ii) glyceryl stearate, (iii) cetearyl alcohol, and (iv) mixtures thereof, relative to the total weight of the emulsifying system, and
   wherein the lipophilic phase (a)/emulsifying system (b) weight ratio is from 0.5 to 4.

2. The composition as claimed in claim 1, wherein the amount of lipophilic phase (a) is from 5% to 40% by weight relative to the total weight of the composition.

3. The composition as claimed in claim 1, wherein the hydrocarbon-based oil is a hydrogenated hydrocarbon-based oil.

4. The composition as claimed in claim 1, wherein the paraffinic compound is chosen from isoparaffins and normal paraffins, and the naphthenic compound is chosen from cycloalkanes comprising 12 to 29 carbon atoms.

5. The composition as claimed in claim 1, wherein the hydrocarbon-based oil has a content of paraffinic compounds ranging from 40% to 99% by weight, relative to the total weight of the hydrocarbon-based oil.

6. The composition as claimed in claim 1, wherein the hydrocarbon-based oil has a content of naphthenic compounds ranging from 1% to 60% by weight, relative to the total weight of the hydrocarbon-based oil.

7. The composition as claimed in claim 1, wherein the hydrocarbon-based oil has a content of isoparaffins ranging from 30% to 90% by weight, relative to the total weight of the hydrocarbon-based oil.

8. The composition as claimed in claim 1, wherein the hydrocarbon-based oil has a content of normal paraffins ranging from 0.01% to 30% by weight, relative to the total weight of the hydrocarbon-based oil.

9. The composition as claimed in claim 1, wherein the hydrocarbon-based oil comprises from 30% to 90% by weight of isoparaffins, from 0.01% to 30% by weight of normal paraffins and from 1% to 60% by weight of naphthenic compounds, relative to the total weight of the hydrocarbon-based oil.

10. The composition as claimed in claim 1, wherein the emulsifying system (b) comprises at least one lipophilic emulsifier and one hydrophilic emulsifier.

11. The composition as claimed in claim 1, wherein the emulsifying system is constituted of Ceteareth-20, Ceteareth-12, cetearyl alcohol and glyceryl stearate.

12. The composition as claimed in claim 1, having a Phase Inversion Temperature inferior or equal to 62° C.

13. The composition as claimed in claim 1, having a Phase Inversion Temperature ranging from 53 to 62° C.

14. The composition as claimed in claim 1, wherein the hydrocarbon-based oil has a content of aromatic compounds inferior to 500 ppm.

15. The composition as claimed in claim 1, wherein the hydrocarbon-based oil has a kinematic viscosity at 40° C., measured according to standard ASTM D445, ranging from 1 to 12 cSt.

16. The composition as claimed in claim 1, wherein the hydrocarbon-based oil has a pour point, measured according to standard ASTM D97, ranging from 10 to −60° C.

17. A cosmetic or dermatological method comprising application to the skin of an individual of the composition as claimed in claim 1.

18. The method according to claim 17, wherein the composition is a suncare product, a skincare product or a makeup product.

19. A method for producing cosmetic products or dermatological products, wherein the method comprises incorporating the composition as claimed in claim 1 in the formulation of the products.

* * * * *